(12) United States Patent
Abelé

(10) Patent No.: US 8,322,210 B2
(45) Date of Patent: Dec. 4, 2012

(54) ELECTRONIC CIRCUIT FOR MEASURING THE MASS OF BIOLOGICAL MATERIAL AND PROCESS FOR MANUFACTURING THE SAME

(75) Inventor: Nicolas Abelé, Paris (FR)

(73) Assignee: STMicroelectronics SA, Montrouge (FR)

( * ) Notice: Subject to any disclaimer, the term of this patent is extended or adjusted under 35 U.S.C. 154(b) by 1203 days.

(21) Appl. No.: 12/120,073

(22) Filed: May 13, 2008

(65) Prior Publication Data

US 2009/0120193 A1   May 14, 2009

(30) Foreign Application Priority Data

May 14, 2007   (FR) ...................................... 07 03449

(51) Int. Cl.
*G01N 9/02* (2006.01)
(52) U.S. Cl. .......................................... 73/433; 73/32 A
(58) Field of Classification Search .................... 73/433, 73/32 A, 32 R, 649, 64.53, 54.24, 61.75, 73/53.01, 865
See application file for complete search history.

(56) References Cited

U.S. PATENT DOCUMENTS

| | | | | |
|---|---|---|---|---|
| 3,726,128 A | * | 4/1973 | Fiet | 73/30.01 |
| 4,848,139 A | * | 7/1989 | Blake-Coleman et al. | 73/61.75 |
| 5,402,670 A | * | 4/1995 | Wicnienski | 73/32 A |
| 6,987,435 B2 | * | 1/2006 | Ko et al. | 335/78 |
| 7,089,813 B2 | * | 8/2006 | Takeuchi et al. | 73/865 |
| 7,357,039 B2 | * | 4/2008 | Rieder et al. | 73/861.357 |
| 7,385,467 B2 | * | 6/2008 | Stoemmer et al. | 333/189 |
| 7,989,714 B2 | * | 8/2011 | Kresina | 177/210 EM |
| 2002/0194908 A1 | * | 12/2002 | Sparks | 73/204.26 |
| 2004/0150296 A1 | | 8/2004 | Park et al. | |
| 2005/0005676 A1 | | 1/2005 | Crawley et al. | |
| 2006/0071286 A1 | | 4/2006 | Axelrod et al. | |
| 2006/0164186 A1 | * | 7/2006 | Stoemmer et al. | 333/189 |
| 2007/0035200 A1 | * | 2/2007 | Casset et al. | 310/309 |
| 2007/0089519 A1 | | 4/2007 | Hao et al. | |
| 2009/0066170 A1 | * | 3/2009 | Abele | 310/25 |
| 2010/0095774 A1 | * | 4/2010 | Sone et al. | 73/580 |

FOREIGN PATENT DOCUMENTS

WO   2005/100965 A1   10/2005
WO   2006/107961 A2   10/2006

OTHER PUBLICATIONS

Abele, N., et al., "0-Level Vacuum Packaging RT Process for MEMS Resonators," DTIP 2007, Stresa, Italy, Apr. 25-27, 2007, 4 pages.
Schroth, A., et al., "A Resonant Poliyimide-Based Humidity Sensor," Sensors and Actuators B 34, 1996, pp. 301-304.

* cited by examiner

Primary Examiner — Peter Macchiarolo
Assistant Examiner — Samir M Shah
(74) Attorney, Agent, or Firm — Seed IP Law Group PLLC

(57) ABSTRACT

A micro scale includes one substrate forming a first zone constituting a first terminal, one conducting vibrating beam which has two opposite ends affixed on two supporting areas on the substrate, the conductive beam forming a second terminal; wherein the conductive beam is made of polymer gel having metallic microparticles in low quantity so as to avoid any contamination of a biological material to measure, the density of the metallic microparticles being high enough to achieve electrical conduction of the second terminal. A manufacturing process of such a micro scale circuit is also provided.

17 Claims, 6 Drawing Sheets

ELECTRONIC CIRCUIT FOR MEASURING THE MASS OF BIOLOGICAL MATERIAL AND PROCESS FOR MANUFACTURING THE SAME

TECHNICAL FIELD

The present disclosure generally relates to the field of microelectronic circuits, and more particularly but not exclusively to an electronic circuit for measuring the mass of biological material and a process for manufacturing the same.

BACKGROUND INFORMATION

Electronic circuits which are suitable for the measurement of mass are known in the art.

FIG. 1 illustrates a first arrangement of a micro scales known in the art which is described in the document "High-Q Longitudinal Block Resonators with Annexed Platform for Mass Sensing Application", by Zhili Hao and Farrokh Ayazi, GTRC No. 3244, 2006 (U.S. Patent Application Publication No. 20070089519). There is disclosed a piezo-electric structure being hanged on two supporting elements or anchors 11 and 12 which also includes two terminals, respectively a drive terminal and a sense terminal. The drive terminal receives an alternating voltage which causes the structure to oscillate. The arrangement further includes two plates, respectively 13 and 14, which can serve as supports for a mass to be measured. The whole arrangement is the equivalent of one resonance circuit, of the type Bulk Acoustic Wave (BAW) operating in a width mode and not in a thickness mode. The effect of the presence of microparticles on plates 13 and 14 causes the resonance frequency to move and such move can be measured by the electronic circuit forming part of one integrated circuit, thanks to the sensing of the current on the sense terminal.

FIG. 2 illustrates a second device which is known in the art and which is described in U.S. Patent Application Publication No. 2004140296 filed on Aug. 5, 2004, entitled: "Material Sensing Sensor and module using thin film bulk accoustic resonator" by Park Jae Yeong, Lee Heon Min, LG ELECTRONICS INC, also based on a BAW type resonator arrangement (Bulk Acoustic Wave) comprising a reference unit associated to a sensing unit receiving the microparticles to measure. Again, the measurement is based on the detection of a change in the resonance frequency and such change allows the calculation of the mass of the microparticles being measured.

All those devices substantially use metal based materials and, consequently, are not suitable for the measurement of masses of biological material which might interfere with metallic material.

BRIEF SUMMARY

Generally speaking, with the development of the scientific techniques falling in the field of biology, it is desirable to have an electronic circuit which is easy to manufacture and which allows the measurement of the weight of biological material.

Such is the goal of one embodiment.

One embodiment provides an arrangement of an electronic circuit which is suitable for the measurement of the weight of biological material.

One embodiment provides an electronic circuit embodying a micro scales which is easy to manufacture and also well fitted to the realization of measurement devices used in the biological field.

One embodiment provides a micro scale for the measurement of a mass which includes:
one substrate forming a first zone constituting a first terminal;
one conducting vibrating beam which has two opposite ends affixed on two supporting areas on said substrate, the conductive beam forming a second terminal;
characterized in that said conductive beam is made of polymer gel comprising metallic microparticles in low quantity so as to avoid any contamination of a biological material to measure, the density of said metallic microparticles being high enough to achieve electrical conduction of said second terminal.

In one particular embodiment, the substrate is silicon and the first terminal is a doped area on the silicon.

Alternatively, the substrate may also be quartz or glass, comprising a first terminal consisting in a conductive layer made in conductive gel.

By incorporating the electric dipole formed by the two terminals or electrodes within one oscillating electronic circuit, one can thus determine the resonance frequency and, therefore, the weight of the material, whatever its form liquid or solid, which weigh on the vibrating beam.

One embodiment also provides a process for manufacturing a micro circuit for the measurement of weights or mass which includes:
preparation of one substrate having one sacrificial oxide layer;
creation of one bottom terminal located on said substrate;
deposit of one gel of active polymer material comprising metallic microparticles in low quantity so as to avoid contamination of biological material to process but dense enough for achieving electrical conduction of said second terminal;
etching of said gel layer in order to form a beam fixed on two anchors located on said substrate;
removing said sacrificial oxide layer so as to release said hanging beam and form a resonating circuit; and
depositing at least one packaging layer.

One embodiment is suitable for the manufacturing of micro scales for the measurement of the weight or the density of biological material flowing in one liquid being in contact with the vibrating beam.

BRIEF DESCRIPTION OF THE SEVERAL VIEWS OF THE DRAWINGS

Other features of one or more non-limiting and non-exhaustive embodiments will best be understood by reference to the following detailed description when read in conjunction with the accompanying drawings.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
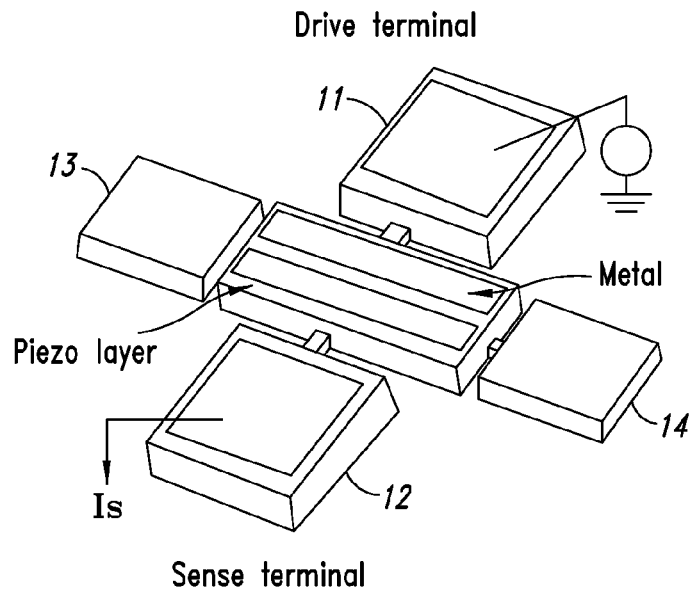
FIGS. 1 and 2 illustrate two microscales known in the art for the measurement of micro particles of material.
Figure 2:
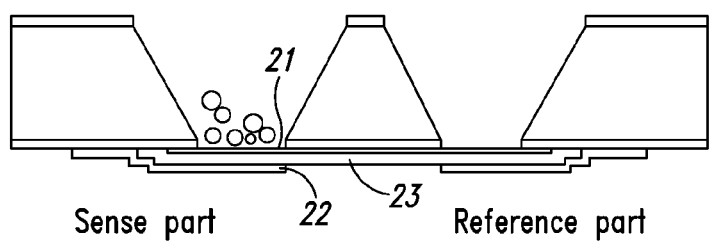
Figure 3:
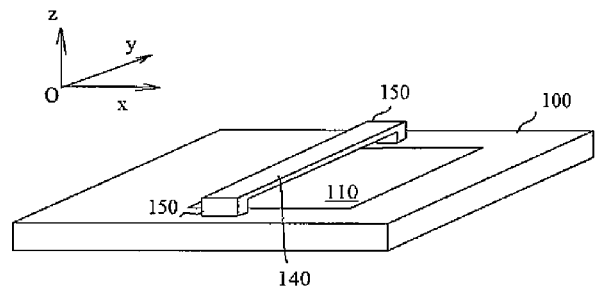
FIG. 3 illustrates one embodiment of a micro scales.
Figure 4:
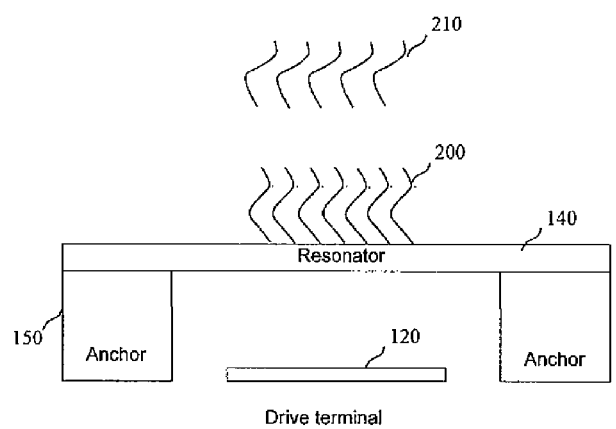
FIG. 4 is an elevation view of the micro-scales according to one embodiment.

FIG. 3 is a perspective view of a micro scale according to one embodiment, comprising one substrate 100 including a first terminal 110 on which is affixed one hanging beam 140 supported at its two opposite ends by two anchors 150 located on substrate 100 and extending along axis O-y.

The micro scale according to one embodiment comprises a hanging beam which is formed by a polymer gel comprising a sufficient concentration of conductive micro-particles so as to constitute a second terminal located above the first terminal which is itself above the substrate.

There is thus carried out a combination of two terminals, respectively bottom and top, the top terminal being likely for form part of one resonator which presents a high value quality factor and which is, moreover, perfectly biocompliant.

The high value of the quality factor allows accurate measurements to be achieved and, further, allows the realization of an efficient micro-scale that is adapted to the measurement of the mass of biological material.

In one particular embodiment, one achieves the suspended beam by means of an electro active polymer such as, for instance, one thin layer polyimide.

Alternatively, one may realize the hanging beam by means of a resonator wherein one introduces conductive particles in order to achieve electrical conduction of the latter.

Generally speaking, the micro-scales circuit which was described above can be carried out by use of different conventional CMOS techniques.

There will now be described a first particular embodiment of a micro scale circuit in reference to FIGS. 5a to 5d, which is based on a semiconductor substrate, for instance of the silicon type 100. In this disclosure, the preliminary techniques which are involved in the preparation of the substrate and which are known will not be discussed further.

Figure 5A:
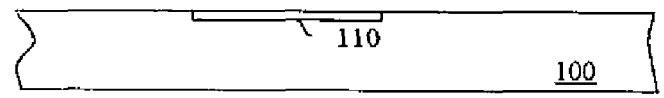
FIGS. 5a to 5d illustrate a first embodiment of a MOSFET transistor made from a conventional substrate.

As shown in FIG. 5a, the process starts with the preparation of a silicon substrate 100, which is doped so as to create a conductive zone used as a bottom terminal 110 which will serve as the drive terminal.

Figure 5B:
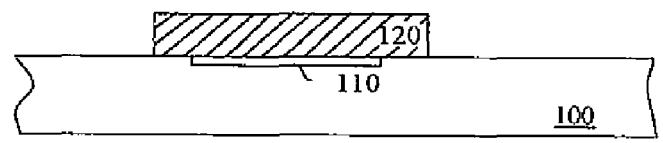

Then, as shown in FIG. 5b, one performs the deposition of a sacrificial oxide layer 120, such as silicon oxide ($SiO_2$), which is then etched with the appropriate profile, e.g., a parallelepiped.

Figure 5C:
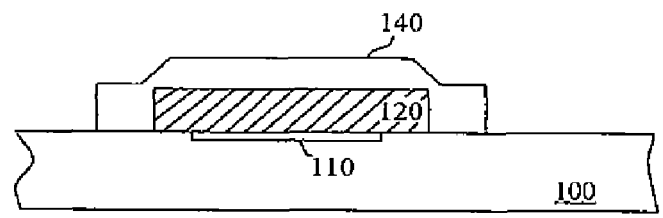
Figure 5D:
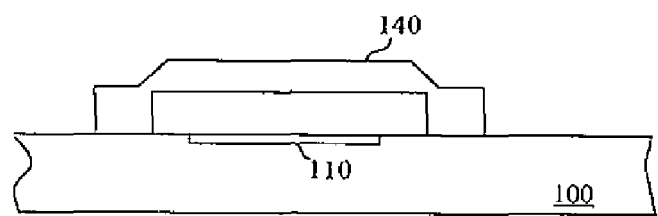

As shown in FIG. 5c, one then performs the deposition of an electro active polymer gel 140, such as polyimide for instance.

This gel deposit can be performed by means of known techniques.

One can for instance perform the deposit of polymer layer 140 by means of a spinning technique. Alternatively, sputtering can also be used for the deposit of deposit polymer 140.

This gel is then etched in order to create the final profile of the resonator, that is to say a beam being affixed at its two ends on two anchors located on substrate 100.

One then eliminates the sacrificial oxide layer 120 by means of known techniques (wet or dry etching) and thus release resonator 140, which forms the functional element of the micro-scales.

One then completes the manufacture of the micro-scale by means of a packaging of the substrate which includes the insertion of the micro-scale described above in a containment volume which can be carried out in different ways in accordance of known techniques which can be used for that purpose.

More development on such techniques may be found in the publication from the inventor, N. Abelé, D. Grogg, C. Hibert, F. Casset, P. Ancey et A. M. Ionescu intitulée "0-level vacuum packaging RT process for MEMS resonators", DTIP 2007, pp. 33-36.

In one particular embodiment, one carries out a package which is adapted for the flow of biological liquid provided by a micro inlet on the micro scale for the purpose of achieving measurement of the density of the liquid.

When the manufacturing process is completed, the micro scale is introduced in one electronic circuit which determines the resonance frequency of the resonator and which closely depends on the mass of the liquid which bears on beam 140. Practically, one inserts the two poles formed by terminals 110 and 140 in one oscillating loop using one amplifier and the oscillation frequency of that loop is measured in order to determine the resonance frequency. Such electronic circuits fitted for that frequency measurement are well known and, therefore, will not be described in detail.

The measurement of the resonance frequency $f_0$ leads to the determination of mass m of the material which pushes down on the flexible beam, in accordance with the formula:

$$f_0 = \frac{1}{2\pi}\sqrt{\frac{k}{m}}$$

with k being the rigidity of the structure.

There is now described a second embodiment of a micro scale circuit which uses, instead of a silicon substrate, a non-conductive substrate such as quartz or glass.

In this second embodiment, one deposits on the quartz or glass substrate a first conductive layer of polymer gel. This first layer is deposited as a thin layer by means of known spinning techniques, which are then patterned.

One then deposits a sacrificial oxide layer, such as silicon oxide ($SiO_2$).

There is then deposited a second layer of conductive polymer which is then etched, as mentioned above, in order to take the profile of a beam forming the resonator. The second layer of polymer can use the same or a different material than the one which was used for the first layer.

One then performs the release of the resonator by eliminating the sacrificial oxide layer, thus completing the functional part of the micro scale.

The packaging operation can then be performed as described above for the first embodiment.

FIGS. 6a-6i show in detail one particular embodiment of a micro scale located on a doped substrate.

Figure 6A:
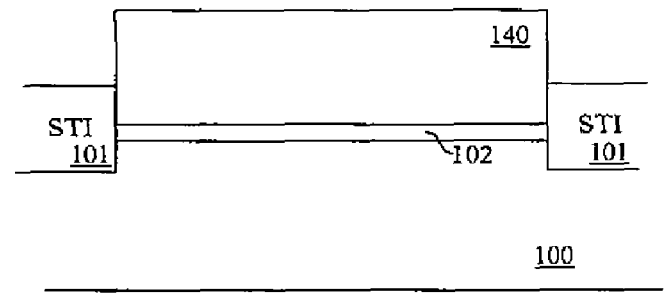
FIGS. 6a to 6i illustrate the detail of the first embodiment of one circuit, manufactured from a Silicon On Insulator (SOI) substrate.

As illustrated in FIG. 6a, the process starts with the preparation of one conventional substrate or bulk 100, fitted with Shallow Trench Insulator (STI) trenches 101 which allow the electric insulation of the different structures located on the same bulk.

The so-called STI technique is well known and, therefore, will not be discussed further. Substrate 100 is, for instance, monocrystal silicon (Si), which is covered by a sacrificial oxide layer 102, such as silica (SiO2).

One then performs the deposition of one active polymer layer 140.

Figure 6B:
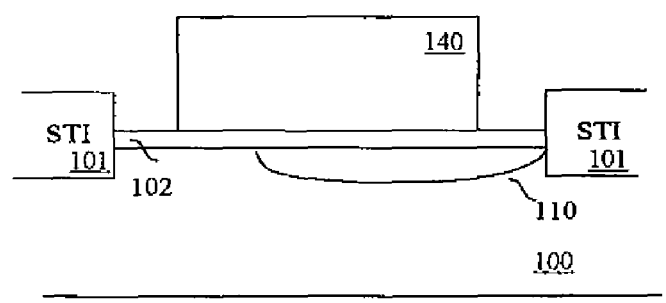

In a subsequent operation, as illustrated in FIG. 6*b*, that polymer layer 140 is etched in order to create the structure of the hanging beam. The anchors or supporting elements of the hanging beam are not shown in the drawing since those are located on both sides of the plane of FIG. 6*b*, ahead and backwards, and are located on the STI zones or even directly on the silicon substrate 100 after a selective etching of the oxide area.

The implant zone is then created so as to embody the first terminal 110, located under layer 140. Clearly, any type of implantation, of the type N or P, can be used. Moreover, the doping energy will be adjusted in accordance to the thickness of the oxide layer 102 to go through. If the oxide layer 102 is particularly thick, one may consider a dry etching for instance, prior to the doping operation. Such techniques are well known and will not be elaborated further.

Figure 6C:
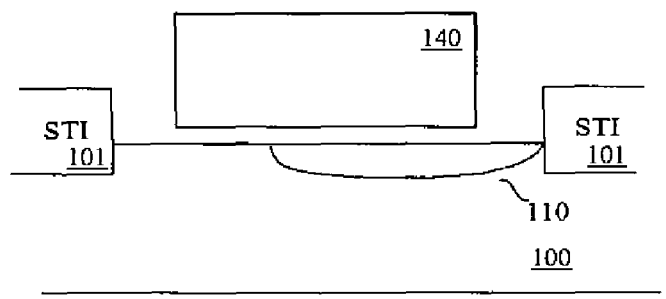

In a subsequent operation, shown in FIG. 6*c*, the sacrificial oxide layer 102 is eliminated by means of any known technique, such as for instance a wet etching based on a BHF acid.

The structure of the gate beam is thus completed and this is then followed by an appropriate packaging operation, such as, for instance, the packaging process s illustrated in FIGS. 6*d* to 6*i*.

Figure 6D:
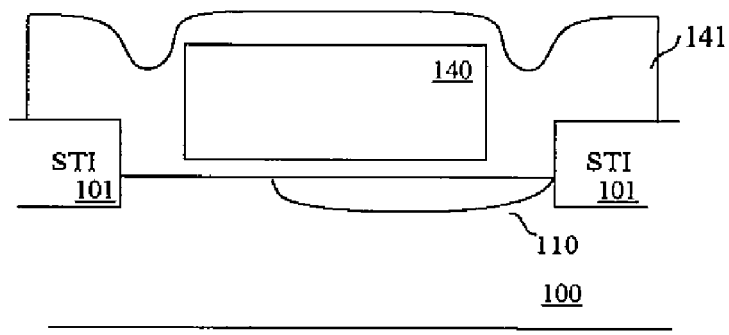

This packaging process includes a sputtering step of amorphous silicon in order to deposit a sacrificial layer 141, as illustrated in FIG. 6*d*. Alternatively, one may deposit a polysilicon conformal layer—i.e., which does not shown any particular orientation—by means of known techniques.

Figure 6E:
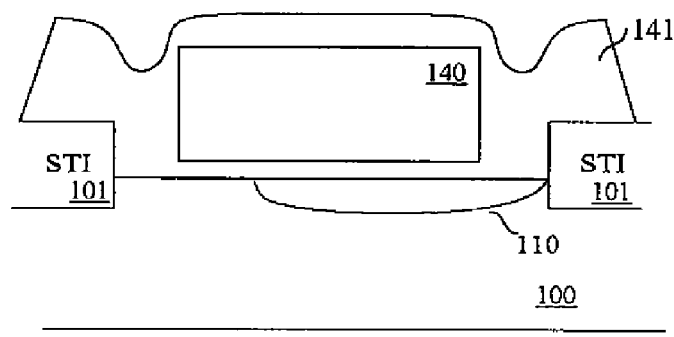

This layer 141 is then etched in order to form two sides on the bias, respectively on the left and on the right, of layer 141, as this is illustrated in FIG. 6*e*.

Figure 6F:
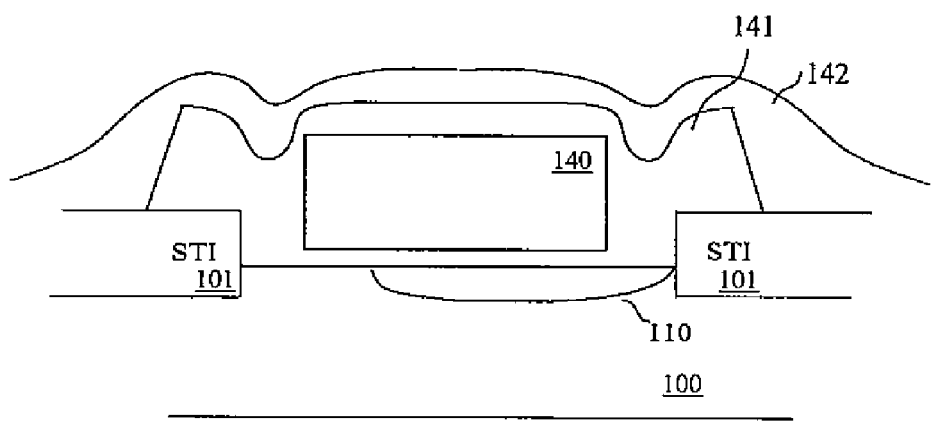

One then proceed with, as illustrated in FIG. 6*f*, with the deposit of a structural layer 142 which permits the cover of the semiconductor product to be fastened, which is carried out by means of the deposit of an appropriate oxide or nitride layer.

Figure 6G:
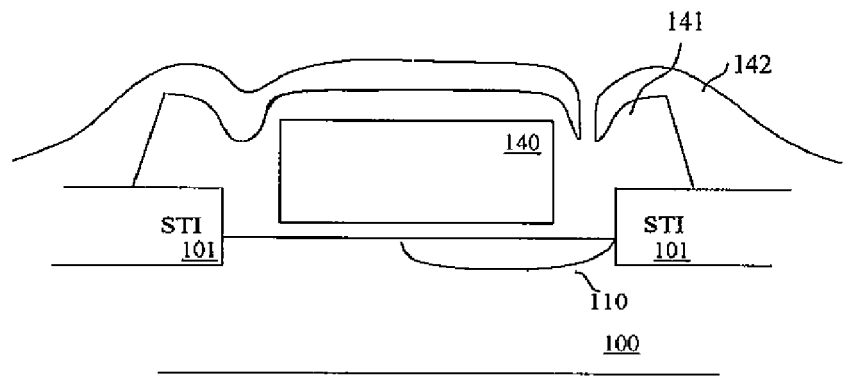
Figure 6H:
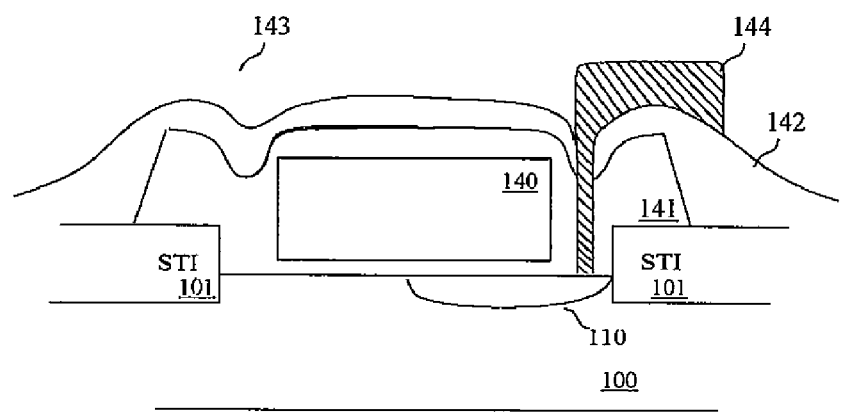
Figure 6I:
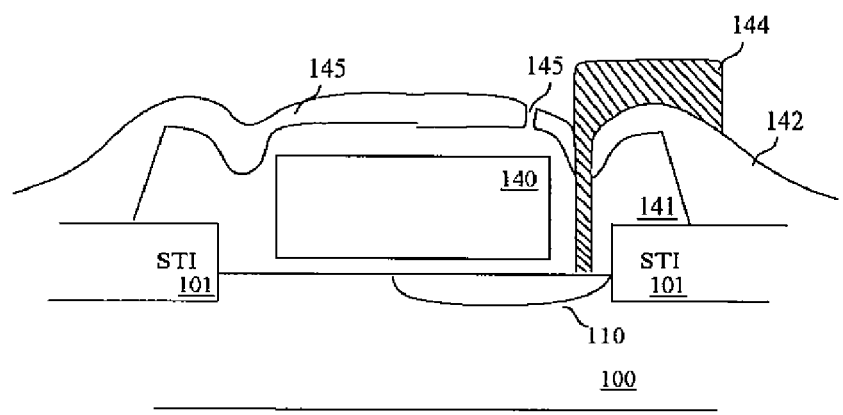

One then proceeds with the opening of a contact via in the doped zone 110, as illustrated in FIG. 6*g*, so as to create the bottom terminal. One also creates one via on one of the anchors of the hanging beam in order to carry out the top terminal (not visible in FIG. 6*g*). One then fills in the via with a conductive polymer 144 in order to create the contact with the bottom terminal of FIG. 6*h*.

One then creates release vias, i.e., small openings 145 allowing to reach the sacrificial layer of amorphous silicon 141, which is then removed by means of known etching techniques.

One then deposits one non conformal oxide layer in order to cover the metallization which were made in the contact vias and also in the openings of the release vias.

The circuit of the micro scale which was described above may be inserted within one electronic oscillating circuit, so as to measure the variation of the resonance frequency which depends on the weight of the material weighing on the top terminal of the resonator.

The micro scale which was described is fully suitable for the measurement of the weight of microparticles. Alternative, this micro scale may serve for the measurement of the density of a liquid made of microparticles of biological material to weigh. In that embodiment, the micro circuit will include one inlet and one outlet for the purpose of the flow of the liquid and have the latter reach the resonator. It should be noticed that, in this particular application of liquid density measurement, the quality factor of the resonator is decreased with respect to the high value which is normally obtained when the beam can resonate in the air.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A micro scale, comprising:
    a substrate;
    a first terminal formed on or in the substrate; and
    a conductive beam which has two opposite ends affixed on two supporting areas on said substrate, said conductive beam constituting a second terminal and being configured to vibrate;
    wherein said conductive beam is made of polymer gel having metallic microparticles in a sufficiently low quantity to avoid any contamination of a biological material to measure, a density of said metallic microparticles being high enough to achieve electrical conduction of said second terminal.

2. The micro scale according to claim 1 wherein said substrate is silicon and wherein said first terminal is a doped area on the silicon.

3. The micro scale according to claim 1 wherein said substrate is either quartz or glass, wherein said first terminal includes a conductive layer made of conductive gel.

4. The micro scale according to claim 1 wherein said micro scale is incorporated in an electronic circuit and allows determination of a resonance frequency.

5. A mass measurement device for measurement of weight or density of a biological material, said measurement device comprising:
    a substrate;
    a first terminal formed on or in the substrate; and
    a conductive beam which has two opposite ends affixed on two supporting areas on said substrate, said conductive beam forming a second terminal and being configured to vibrate;
    wherein said conductive beam includes metallic microparticles in a sufficiently low quantity so as to avoid contamination of said biological material, a density of said metallic microparticles being sufficiently high to achieve electrical conduction of said second terminal.

6. The device according to claim 5 wherein said substrate is silicon and said first terminal is a doped area on the silicon.

7. The device of claim 5 wherein said conductive beam is made from a polymer gel that includes said metallic microparticles.

8. The device of claim 5 wherein said substrate and said conductive beam form a micro scale, the device further comprising an electronic circuit coupled to said micro scale and adapted to determine a resonant frequency of said conductive beam when said biological material is on said conductive beam.

9. The device of claim 5 wherein said substrate is made from a nonconductive material, and wherein said first terminal is made from a conductive gel.

10. The device of claim 5, further comprising a packaging material formed over said conductive beam.

11. An apparatus adapted to measure mass of a biological material, the apparatus comprising:
a substrate;

a first conductive terminal formed on or in the substrate; and a conductive beam that forms a second conductive terminal and having at least one portion anchored to said substrate, wherein said conductive beam includes microparticles of a quantity insufficient to contaminate said biological material, when said biological material is placed on said conductive beam, and wherein said quantity of said microparticles is sufficient to provide said conductive beam with electrical conductivity.

12. The apparatus of claim 11 wherein said substrate is made from a semiconductor material and said first zone is a doped region in said semiconductor material.

13. The apparatus of claim 11 wherein said substrate is made from a nonconductive material, and wherein said first zone is made from a conductive gel on said nonconductive material.

14. The apparatus of claim 13 wherein said nonconductive material includes glass or quartz.

15. The apparatus of claim 11, further comprising a structural layer formed over said conductive beam.

16. The apparatus of claim 11, further comprising a conductive material formed in a via that extends through said structural layer, said conductive material being in electrical contact with said first terminal at a first end and extending past said structural layer at a second end.

17. The apparatus of claim 11 wherein said at least one portion of said conductive beam that is anchored to said substrate includes first and second opposite ends of said conductive beam that are anchored to said substrate.

* * * * *